United States Patent [19]

Agarwal et al.

[11] Patent Number: 5,527,949

[45] Date of Patent: Jun. 18, 1996

[54] METHOD FOR MAKING AN AMINE AND AN ALKYL ESTER AND METHOD FOR REDUCING HYDROGEN CYANIDE LEVELS IN ALKYL ESTER

[75] Inventors: Sudhir K. Agarwal; Rajiv M. Banavali, both of Houston; Bharati D. Chheda, Spring; Samuel F. Reed, Jr., Seabrook, all of Tex.

[73] Assignee: Rohm and Haas Company, Philadelphia, Pa.

[21] Appl. No.: 294,680

[22] Filed: Aug. 23, 1994

[51] Int. Cl.⁶ .................................................. C07C 67/00
[52] U.S. Cl. .................. 560/129; 560/239; 560/247; 560/248; 564/468; 564/490
[58] Field of Search .................................. 560/232, 239, 560/248, 265, 247, 129; 564/468, 490

[56] References Cited

U.S. PATENT DOCUMENTS

| 3,821,220 | 6/1974 | Daugherty et al. | 260/249.6 |
| 4,131,642 | 12/1978 | Miller et al. | 423/193 |

FOREIGN PATENT DOCUMENTS

| 50871 | 10/1980 | European Pat. Off. | C07C 87/02 |
| 50868 | 10/1981 | European Pat. Off. | C07C 85/20 |
| 0050868 | 5/1982 | European Pat. Off. | |
| 99752 | 7/1983 | European Pat. Off. | |
| 0099752 | 1/1984 | European Pat. Off. | C07C 102/08 |

OTHER PUBLICATIONS

Lucas, Organic chemistry 2ed., 1953 p. 141.

*Primary Examiner*—José G. Dees
*Assistant Examiner*—Rosalynd A. Williams
*Attorney, Agent, or Firm*—Darryl P. Frickey

[57] ABSTRACT

A method for making an amine includes the steps of heating a reaction mixture including a nitrile, an acid, water and a substrate compound capable of generating a carbonium ion by reaction with the acid to generate a first reaction intermediate; treating the first reaction intermediate with an acid in the presence of a primary alkanol to form a second reaction intermediate and an alkyl ester; separating the alkyl ester from the second reaction intermediate; and treating the second reaction intermediate with a base to form the amine.

11 Claims, No Drawings

METHOD FOR MAKING AN AMINE AND AN ALKYL ESTER AND METHOD FOR REDUCING HYDROGEN CYANIDE LEVELS IN ALKYL ESTER

The present invention relates to a method for making an amine and an alkyl ester.

Methods for making amines wherein an alkene is reacted with hydrogen cyanide to form a formamide, which is subsequently hydrolyzed into the corresponding amine and formic acid are known.

European Patent Application, Publication No. 0 050 871 discloses a method wherein an N-tert-alkyl amine or a cycloalkylamine and an ester of formic acid and a primary or secondary alcohol are directly and simultaneously formed by reacting an alkene with a hydrogen cyanide in the presence of a strong acid and a primary or secondary alcohol.

While the method of the '871 document is said to provide improved yield of amine relative to that of earlier methods, there are several disadvantages associated with the method disclosed in the '871 document. The method of the '871 document introduces an inefficiency in that, for a given reaction vessel used in a batch process, the batch size must be reduced in order to accommodate the added alcohol charge. Furthermore, it appears, based on the procedures set forth in the Examples of the '871 document, that it is necessary to provide cooling of the reactor contents to the control reaction temperature during the initial stages of the reaction in order to maintain the disclosed improvement in the yield of amine. Finally, the process of the '871 document provides no teaching regarding removal of process impurities, such as, for example, hydrogen cyanide and water, from the formate ester by-product.

A method for making an amine is disclosed. The method includes the steps of heating a reaction mixture including a nitrile, an acid, water and a substrate compound capable of generating a carbonium ion by reaction with the acid to generate a first reaction intermediate; contacting the first reaction intermediate with an acid in the presence of water and an alkanol to form a second reaction intermediate and an alkyl ester; separating the alkyl ester from the second reaction intermediate; and contacting the second reaction intermediate with a base to form the amine. The method provides high respective yields of amine and alkyl ester without compromising batch size and does not require cooling to control the reaction temperature.

In a preferred embodiment of the method, the alkyl ester is treated with a metal alkoxide, subsequent to separating the alkyl ester from the tertiary alkyl ammonium salt, The treatment reduces the respective levels of hydrogen cyanide and water impurities in the alkyl ester, In a first step of the method of the present invention, a nitrile and a substrate capable of generating a carbonium ion by reaction with a strong acid are heated in the presence of water and a strong acid HA to generate a first reaction intermediate.

Suitable substrate compounds for the method of the present invention are those known as substrates for the Ritter reaction and include, for example, alcohols, alkenes, aldehydes, ketones, ethers, see, generally, L. I. Krimen and D. J. Cota, "The Ritter Reaction", *Organic Reactions*, Vol. 17, 1969, pp. 213–325.

In a preferred embodiment, the substrate compound is an alcohol. Suitable alcohols include, for example, benzyl alcohol, isopropanol, cyclohexanol, t-butanol, t-amyl alcohol, t-octanol and α-terpineol.

In an alternative preferred embodiment, the substrate is an alkene, more preferably, an alkene according to the structural formula (1):

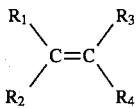

(1)

wherein:

$R_1$ and $R_2$ are each independently $(C_1-C_{10})$alkyl, substituted $(C_1-C_{10})$alkyl, $(C_1-C_{10})$ alkenyl or substituted $(C_1-C_{10})$alkenyl; and $R_3$ and $R_4$ are each independently hydrogen or $(C_1-C_{10})$alkyl, substituted $(C_1-C_{10})$alkyl, $(C_1-C_{10})$alkenyl or substituted $(C_1-C_{10})$alkenyl;

or, alternatively, $R_1$ and $R_3$ are joined to form, together with the alkenyl carbons to which they are attached, a $(C_4-C_{10})$ cycloalkenyl ring or a substituted $(C_4-C_{10})$cycloalkenyl ring; and $R_2$ and $R_4$ are each independently hydrogen, $(C_1-C_{10})$alkyl or substituted $(C_1-C_{10})$alkyl.

As used herein, the terminology "$(C_1-C_{10})$alkyl" means a straight-chain or branched alkyl group having from 1 to 10 carbon atoms per group.

As used herein, the terminology "$(C_4-C_{10})$cycloalkenyl ring" means a cyclic alkenyl ring having from 4 to 10 carbon atoms per ring.

Suitable alkenes according to structural formula (1) include, for example, isobutene, 2,3-dimethyl-2-butene, 2,3-dimethyl-1-pentene, 2,3-diethyl-1-hexene, 2-methyl-3-ethyl-1-pentene, 2,3,3-trimethyl-1-heptene, 2,3,3,4-tetramethyl-1-hexene, 2,3-dimethyl-1,3-butadiene, 2,5-dimethyl-1,5-hexadiene, 1,3,9-trimethyl cyclododeca-1,3,9-triene, myrcene, cyclohexene, cycloheptene, cyclooctene, terpenes, such as, for example, limonene, α-terpineol and Δ-carene, alkene oligomers and mixtures thereof. As used herein, the terminology "alkene oligomer" means a compound consisting of a linear, branched or cyclic chain of front 2 to about 20 repeating units derived by polymerizing alkene monomers. Suitable alkene oligomers include, for example, dimers; trimers, tetramers and pentamers of propylene, butylene, isobutylene and isoprene, such as, for example, butylene dimer, isobutylene dimer, propylene trimer, propylene tetramer, butylene tetramer, isobutylene tetramer, propylene hexamer and mixtures thereof.

In a preferred embodiment, the substrate compound has more than one reactive site per molecule capable of generating a carbonium ion, including, for example, α-terpineol, limonene and dimethyl-1,3-butadiene.

In a highly preferred embodiment, the substrate compound is an alkene selected front the group consisting of propylene tetramer, propylene hexamer and isobutylene dimer.

In a preferred embodiment, the strong acid HA is a compound that has a pKa less than about 5, more preferably less than about 2. Suitable strong acids include inorganic acids such as, for example, hydrochloric acid, phosphoric acid, perchloric acid, organic acids such as, for example, formic acid, methane sulfonic acid, p-toluene sulfonic acid and strongly acidic ion exchange resins such as, for example, Amberlyst 15 (Rohm and Haas Company, Philadelphia, Pa.).

In a highly preferred embodiment, the strong acid HA is a concentrated aqueous solution of sulfuric acid that includes from about 60 wt % to about 100 wt % sulfuric acid.

The reaction mixture includes from about 0.2 moles to about 4 moles, more preferably front about 1 moles to about 2 moles, of the strong acid HA per mole of reactive sites of the substrate compound, wherein the number of moles of reactive sites of the substrate compound equals the product of the number of moles of substrate compound multiplied by the number of reactive sites per molecule of the substrate compound.

The nitrile may be any compound of the structural formula (2):

$$R_5-C\equiv N \qquad (2)$$

wherein $R_5$ is H, $(C_1-C_5)$alkyl, vinyl or phenyl.

As used herein, the terminology "$(C_1-C_5)$alkyl" means a straight-chain or branched alkyl group having from 1 to 5 carbon atoms per group, such as, for example, methyl, ethyl, propyl, n-butyl, t-butyl t-pentyl.

Suitable nitriles include hydrogen cyanide, acetonitrile, butyl nitrile, acrylonitrile and benzonitrile. Preferably, the nitrile is hydrogen cyanide.

Preferably, the nitrile is added directly to the reaction mixture. Alternatively, the nitrile may be generated in situ by adding a compound which forms a nitrile under the reaction conditions of the present invention to the first reaction mixture.

In a preferred embodiment, hydrogen cyanide is added directly to the reaction mixture as the nitrile. In an alternative embodiment, a compound which generates hydrogen cyanide under the reaction conditions of the present process is added to the reaction mixture and hydrogen cyanide is generated in situ. Suitable hydrogen cyanide-generating compounds include, for example, cyanide salts such as, for example, sodium cyanide, potassium cyanide.

The reaction mixture includes from about 1 mole to about 10 moles, more preferably from about 1 mole to about 1.5 moles, nitrile or an equivalent amount of nitrile-generating compound per mole of reactive sites of the substrate.

The reaction mixture of the first step of the process includes from about 0.8 mole to about 10 moles, more preferably from about 1 mole to about 3 moles, water per mole of reactive sites of the substrate.

The reaction mixture is maintained at a temperature from about 20° C. to about 120° C., more preferably, front about 30° C. to about 60° C., during the first process step. In a preferred embodiment, the substrate compound is charged to the reaction vessel and the acid and nitrile are fed into the reaction vessel according to feed rate profiles that allow heating of the reaction mixture by reaction exotherm to a selected temperature.

The reaction mixture is maintained at a pressure from about 1 atmosphere to about 10 atmospheres, preferably about 1 atmosphere, during the first process step.

The first reaction intermediate is not isolated front the reaction mixture. While not wishing to be bound by theory, it is believed that in the preferred embodiment, wherein the substrate is an alkene according to the structural formula (1), the first reaction intermediate is an amidinium salt having the structural formula (3):

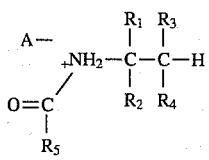

wherein

A—is the residue of the acid HA, and $R_1$, $R_2$, $R_3$, $R_4$ and $R_5$ are each as defined above.

In a second process step, the first reaction intermediate is treated with a strong acid HA' in the presence of water and an alkanol of the structural formula (4):

$$R_6-OH \qquad (4)$$

wherein $R_6$ is $(C_1-C_8)$alkyl, $(C_4-C_8)$ cycloalkyl, or benzyl, to form a second reaction intermediate and an alkyl ester of the structural formula (5):

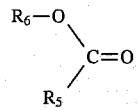

wherein $R_5$ and $R_6$ are each as defined above.

As used herein, "$(C_1-C_8)$alkyl" means a straight-chain or branched alkyl group having from 1 to 8 carbon atoms per group.

As used herein, "$(C_4-C_8)$cycloalkyl" means an alkyl ring having from 4 to 8 carbon atoms per ring.

Suitable alkanols include, for example, methanol, ethanol, butanol, propanol, isopropanol cyclohexanol, t-butanol and benzyl alcohol.

In a highly preferred embodiment, the alkanol is selected from the group consisting of methanol and ethanol.

The reaction mixture of the second step of the process includes from about 0.5 mole to about 20 moles, more preferably from about 1 mole to about 10 moles, water per mole of reactive sites of the substrate compound.

The second reaction intermediate is not isolated from the reaction mixture. While not wishing to be to bound by theory, it is believed that in the preferred embodiment wherein the substrate is an alkene according to the structural formula (1), the second reaction intermediate is an ammonium salt having the structural formula (6):

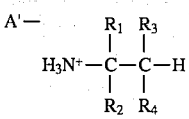

wherein:

A'—is the residue of the acid HA', and $R_1$, $R_2$, $R_3$, and $R_4$ are each as defined above.

In a preferred embodiment, from about 1 mole to about 10 moles, more preferably form about 1 mole to about 4 moles, alkanol per mole of nitrile is added to the reaction mixture in the second process step.

Suitable strong acids HA' are those disclosed above as being suitable for acid HA, with concentrated sulfuric acid being preferred as HA'.

The reaction mixture is gradually heated to a temperature of from about 50° C. to about 130° C., preferably about 60° C. to about 110° C., during the second process step.

The reaction mixture is maintained at a pressure from about 0.1 to about 2 atmospheres, preferably about 1 atmosphere, during the second process step.

In a third process step, the alkyl ester is separated from the second reaction intermediate, preferably by distillation. The separation may, optionally, take place concurrently with the second process step.

In a fourth process step, the second reaction intermediate is neutralized with a strong base to form the amine.

In the preferred embodiment wherein the substrate is an alkene according to the structural formula (1), the amine is a compound according of the structural formula (7):

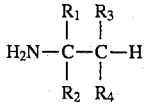

wherein $R_1$, $R_2$, $R_3$, and $R_4$ are each defined as above.

Suitable strong bases are those having a pKa of greater than or equal to about 8 and include, for example, ammonium hydroxide, sodium hydroxide, potassium hydroxide, aqueous ammonia, with sodium hydroxide and aqueous ammonia being preferred.

In the preferred embodiment of the process of the present invention wherein the nitrile is hydrogen cyanide, the alkyl ester includes hydrogen cyanide and water as impurities, e.g., at a level of from about 0.1 wt % hydrogen cyanide to about 3 wt % hydrogen cyanide in the alkyl ester distillate.

In a further aspect of the present invention, we have found that the level of hydrogen cyanide and water contamination of the alkyl ester may be dramatically reduced, i.e., to selected levels down to below the limit of detection, i.e., below about 10 parts per billion (ppb), by treatment of the alkyl ester with a metal alkoxide.

In a preferred embodiment of the present invention the alkyl ester is contacted with a metal alkoxide to convert the hydrogen cyanide-contaminant to a metal cyanide salt and an alkanol and the alkyl ester is then separated from the metal cyanide salt and the alkanol, to thereby provide an alkyl ester having a reduced level of hydrogen cyanide contaminant.

In a preferred embodiment, the metal alkoxide is of the structural formula (8):

$$M{-}(O{-}R_7)_n \qquad (8)$$

wherein

M is a metal cation;

$R_7$ is $(C_1-C_{10})$alkoxyl; and n is an integer from 1 to 4.

As used herein, the terminology "metal cation" means a metal ion having a positive charge, such as, e.g., positively charged ions of zinc, titanium, sodium, potassium, lithium, aluminum, silicon and antimony.

The term "$(C_1-C_{10})$alkyl" means a straight-chain or branched alkyl group having from 1 to 10 carbon atoms per group, including, for example, methyl, ethyl, n-butoxyl, t-butyl, t-pentyl, heptyl, nonyl. Preferably, $R_7$ is $(C_1-C_6)$alkyl.

Suitable metal alkoxides include, for example, sodium methoxide, potassium ethoxide, lithium t-butoxide, potassium t-butoxide, sodium t-pentoxide, triisopropoxy titanate and tetramethoxy silane. Mixtures of metal alkoxides are also suitable. In a highly preferred embodiment, the metal alkoxide is sodium methoxide or potassium t-butoxide.

Polymeric metal alkoxides, such as, for example, poly(dimethoxy siloxane), poly(dibutyl titanate) and poly(antimony ethylene glycoside) are also suitable as the metal alkoxide.

In a preferred embodiment, the metal alkoxide is generated by treating a metal with excess alcohol to form a solution of the metal alkoxide in the alcohol, for example, by treating sodium with excess methanol to form solution of sodium methoxide in methanol. Suitable alcoholic solutions of metal alkoxides may be generated using one or more metal compounds in combination with one or more alcohols.

The hydrogen cyanide-contaminated alkyl ester is contacted with the metal alkoxide, e.g., by agitating a mixture of the hydrogen cyanide-contaminated alkyl ester and the metal alkoxide or by passing the alkyl ester through a fixed or fluidized bed comprising the metal alkoxide.

In a preferred embodiment, the alkyl ester is contacted with the metal alkoxide by agitating a mixture of the hydrogen cyanide-contaminated alkyl ester and the metal alkoxide.

In a preferred embodiment, the metal alkoxide is introduced into the hydrogen cyanide-contaminated alkyl ester as a solution of the metal alkoxide in an organic solvent or a mixture of organic solvents. Suitable organic solvents are those that are either identical to the alkyl ester to be treated or miscible with and readily separable, for example, by distillation, from the alkyl ester to be treated. Suitable organic solvents include, for example, alkyl esters, methanol, ethanol, tetrahydrofuran and diethyl ether.

In a highly preferred embodiment, the metal alkoxide is introduced into the alkyl ester to be treated as a solution in an alkyl ester that is identical to the alkyl ester to be treated.

In a first alternative highly preferred embodiment, solid phase metal alkoxide is added directly to the hydrogen cyanide-contaminated alkyl ester.

In a second alternative highly preferred embodiment, the metal alkoxide is introduced into the hydrogen cyanide-contaminated alkyl ester as a solution of the metal alkoxide in its corresponding alcohol.

In a preferred embodiment, the alkyl ester is contacted with an excess, based on the molar amount of hydrogen cyanide contaminant in the alkyl ester, of the metal alkoxide.

In a highly preferred embodiment, the organic liquid is contacted with an molar excess of about 10% to about 300% of the metal alkoxide, based on moles of hydrogen cyanide in the hydrogen cyanide-contaminated alkyl ester to be treated.

In a preferred embodiment, the mixture is agitated at a temperature from about 0° C. to about 100° C., more preferably from about 20° C. to about 60° C.

The hydrogen cyanide-contaminated alkyl ester is contacted with the metal alkoxide for a period of time that is effective under the treatment conditions to allow conversion of the hydrogen cyanide impurity to a metal cyanide salt and an alkanol. The contact time required is dependent upon the treatment temperature, the initial level of hydrogen cyanide contained in the alkyl ester, the amount of metal alkoxide used and the target level of hydrogen cyanide in the purified alkyl ester. In a preferred embodiment, the mixture of hydrogen cyanide-contaminated organic alkyl ester and metal alkoxide is agitated for a time period of about 1 minute to about 4 hours, more preferably, from about 5 minutes to about 1 hour.

Subsequent to conversion of the hydrogen cyanide impurity to a metal cyanide salt and an alkanol, the metal alkoxide-treated alkyl ester is separated, e.g., by distillation, liquid-liquid extraction or filtration, from the metal cyanide salt and the alkanol, as well as from any organic solvent used to introduce the metal alkoxide, to provide a purified alkyl ester. The appropriate separation method is selected in a known way based on the respective physical and chemical properties of the compounds to be separated.

In a preferred embodiment, the metal alkoxide-treated alkyl ester is distilled to provide the purified alkyl ester.

EXAMPLES 1–4

The hydrogen cyanide content of the alkyl esters of Examples 1–4 was measured using the following method:

An HP 5890 Gas Chromatograph Hewlett-Packard) equipped with a HP-FFAP crosslinked, 0.2 mm diameter, 25 meter long fused silica capillary column having a 0.3 micrometer film thickness (Hewlett-Packard) and a split/splitless injector was used to separate the sample and a Nitrogen-Phosphorous detector (Hewlett-Packard Part No. 19234-60560) was used to detect the level of nitrogen in the column effluent.

The apparatus was calibrated using a serial dilution of hydrogen cyanide in methyl formate.

Measurements were made using a 1 microliter sample size. The injector and detector were each run at 150° C. Helium was used as the carrier gas at a flow rate of front 1 milliliter to 4 milliliters per minute.

EXAMPLE 1

An alkene (194.6 grams (g) propylene tetramer) was charged to a 1 liter 4-necked reaction vessel that was equipped with heating mantle, a thermometer, a mechanical stirrer, a reflux condenser, a nitrile feed buret and an acid feed buret. A nitrile (33.2 g hydrogen cyanide) and a strong acid (154.2 g 87% aqueous sulfuric acid) were each fed into the reaction vessel at respective rates effective to heat the contents of the reaction vessel to about 40° C. due to reaction exotherm alone and to then maintain the contents of reaction vessel at that temperature during the remainder of the addition. The mixture was stirred and maintained at 40° C. for a total of 2 hours.

After the 2 hour period, the burets were removed from the reaction vessel and the reaction vessel was then equipped with a Dean-Stark trap fitted with a reflux condenser. An alkanol (66 g methanol) and water (108 g) were then added to the reaction vessel and the mixture was then heated and refluxed with agitation at 95° C. for 3.5 hours. After 3.5 hours, hydrolysis overhead was removed to raise the temperature of the reaction mixture gradually to 107° C., for a total reflux period of 4.5 hours.

The reaction mixture was then cooled to room temperature. The Dean-Stark trap and condenser assembly was then replaced by an aqueous ammonia addition funnel. The reaction mixture was neutralized by slowly adding 234 g aqueous ammonia to the reaction mixture while maintaining the temperature of the mixture at 60° C. Stirring was discontinued and the reaction mixture was allowed to separate into an organic liquid layer and an aqueous liquid layer. The layers were then separated to provide an organic layer of 193.9 g. The organic layer had a neutral equivalent of 211 and include 2.6 wt % water.

The organic layer was distilled to provide 177.8 g of the amine product (99.2% of theoretical yield).

The hydrolysis overhead was separated into an organic layer (55.9 g) and an aqueous layer (83.6 g). The aqueous layer included methanol, methyl formate, hydrogen cyanide and propylene tetramer.

The aqueous layer of the hydrolysis overhead was charged to a 2-necked round bottom flask. The flask was fitted with a 10 tray Oldershaw distillation column, a reflux condenser and a receiver. The aqueous layer was then distilled to separate the components of the layer. The first distillate cut (24.6 g) was taken at vapor temperatures front 31° C. to 33° C. and included about 95 wt % methyl formate, about 3 wt % methanol and 0.5 wt % hydrogen cyanide. The distillation residue separated into a methanol-rich layer and a propylene tetramer-rich layer. The methanol-rich layer and a propylene tetramer-rich layer were then separated in a separatory funnel.

EXAMPLE 2

Isobutylene dimer was used as the alkene in a process substantially identical to that set forth above in Example 1. The details of the isobutylene dimer process are set forth below.

73.8 g isobutylene dimer, 19.4 g hydrogen cyanide and 114.8 g 75% sulfuric acid were charged to the reaction vessel in the generation step and 206.8 g methanol and 108 g water were added in the hydrolysis step.

428 g aqueous ammonia were used to neutralize the product mixture to provide 93 g of an organic layer having a neutral equivalent of 138 and a water content of 7.32 wt %. The organic layer yielded 82 g of t-octyl amine (97.9% of theoretical yield) upon distillation.

Hydrolysis overhead was separated into an organic layer (55.9 g) and an aqueous layer (83.6 g). The aqueous layer contained methanol, methyl formate and isobutylene dimer. The aqueous layer of the hydrolysis overhead was distilled to yield 33 g of a first cut (taken at vapor temperatures from 31° C. to 33° C.) that contained about 95 wt % methyl formate, about 3 wt % methanol and 0.5 wt % hydrogen cyanide.

EXAMPLE 3

24.6 g of the distillate fraction of the hydrolysis overhead of Example 1 was transferred to a 3-necked round-bottomed flask. The flask was fitted with a Vigreux column, a condenser and a receiver. 2 molar equivalents (based on amount of hydrogen cyanide) of sodium methoxide was added to the flask as a solution of 25 wt % sodium methoxide in methanol and the resultant mixture was agitated vigorously for 10 minutes.

The mixture was distilled to provide 16 g of methyl formate (97% purity) that contained less than 1.0 part per million (ppm) hydrogen cyanide.

EXAMPLE 4

33 g of the distillate fraction of the hydrolysis overhead of Example 2 was treated with sodium methoxide according to the procedure set forth above in Example 3 to yield 18 g methyl formate (97% purity) that contained less than 1.0 ppm hydrogen cyanide.

We claim:

1. A process for making an amine and an alkyl ester, comprising:

heating a reaction mixture comprising a nitrile, an acid, water and a substrate compound being capable of generating a carbonium ion by reaction with the acid, to generate a first reaction intermediate in the reaction mixture;

contacting the first reaction intermediate in the reaction mixture with an acid in the presence of an alkanol to form a second reaction intermediate and an alkyl ester;

separating the alkyl ester from the second reaction intermediate; and contacting the second reaction intermediate with a base to form the amine.

2. The method of claim 1, wherein the substrate compound is selected from the group consisting of alcohols, alkenes, cycloalkenes and mixtures thereof.

3. The method of claim 1, wherein the nitrile is hydrogen cyanide.

4. The method of claim 1, wherein the acid is sulfuric acid.

5. The method of claim 1, wherein the alkanol is ethanol or methanol.

6. The process of claim 1, wherein the alkyl ester contains hydrogen cyanide as a contaminant, further comprising, subsequent to the step of separating the alkyl ester from the second reaction intermediate, contacting the alkyl ester with a metal alkoxide to convert the hydrogen cyanide to a metal cyanide salt and an alkanol; and separating the alkyl ester front the metal cyanide salt and the alkanol, to thereby provide an alkyl ester having a reduced level of hydrogen cyanide contaminant.

7. The process of claim 6, wherein the step of contacting comprises adding a solution of the metal alkoxide in an alcohol to the alkyl ester to form a mixture and agitating the mixture.

8. The method of claim 6, wherein the step of separating the alkyl ester from the metal cyanide salt and the alkanol comprises distilling the alkyl ester.

9. The method of claim 6, wherein the metal alkoxide is a compound of the structural formula:

$$M(O-R_7)_n$$

wherein:

M is a metal cation;

$R_7$ is $(C_1-C_{10})$alkyl; and n is an integer from 1 to 4.

10. The method of claim 9, wherein the metal alkoxide is selected from the group consisting of sodium methoxide and potassium t-butoxide.

11. The method of claim 6, wherein the alkyl ester is contacted with an molar excess of about 10% to about 300% of the metal alkoxide, based on moles of hydrogen cyanide contaminant initially contained in the alkyl ester.

* * * * *